United States Patent [19]

Ford et al.

[11] Patent Number: 5,342,969

[45] Date of Patent: Aug. 30, 1994

[54] RECOVERY OF HYDROXYCARBOXYLIC ACID VALUES FROM POLY(HYDROXYCARBOXYLIC ACIDS)

[75] Inventors: Thomas M. Ford, Greenville, Del.; James V. Tarbell, Hockessin, both of Del.

[73] Assignee: E. I. Du Pont de Nemours and Company, Wilmington, Del.

[21] Appl. No.: 25,923

[22] Filed: Mar. 3, 1993

[51] Int. Cl.$^5$ ............................................. C07D 319/12
[52] U.S. Cl. ...................................... 349/274
[58] Field of Search ......................................... 549/274

[56] References Cited

U.S. PATENT DOCUMENTS

| | | | |
|---|---|---|---|
| 1,095,205 | 5/1914 | Gruter | 549/274 |
| 2,668,162 | 2/1954 | Lowe | 260/78.3 |
| 2,703,316 | 3/1955 | Schneider | 260/78.3 |
| 3,297,033 | 1/1967 | Schmitt et al. | 128/335.5 |
| 3,322,791 | 5/1967 | Selman | 260/340.2 |
| 4,279,249 | 7/1981 | Vert et al. | 128/92 |
| 4,300,565 | 11/1981 | Rosensaft et al. | 128/335.5 |
| 4,471,077 | 9/1984 | Lange | 521/64 |
| 4,719,246 | 1/1988 | Murdoch et al. | 521/134 |
| 4,727,163 | 2/1988 | Bellis | 549/274 |
| 4,835,293 | 5/1989 | Bhatia | 549/274 |
| 4,990,222 | 2/1991 | Aigner et al. | 203/91 |
| 5,023,349 | 6/1991 | Bhatia | 549/274 |
| 5,028,667 | 7/1991 | McLain et al. | 525/415 |
| 5,035,522 | 10/1991 | Muller | 549/274 |
| 5,053,485 | 10/1991 | Nieuwenhuis et al. | 528/354 |
| 5,091,544 | 2/1992 | Bhatia | 549/274 |

FOREIGN PATENT DOCUMENTS

| | | |
|---|---|---|
| 1083275 | 5/1960 | Fed. Rep. of Germany . |
| WO9001521 | 2/1990 | PCT Int'l Appl. . |
| WO9116368 | 10/1991 | PCT Int'l Appl. . |

*Primary Examiner*—C. Warren Ivy
*Assistant Examiner*—A. A. Owens

[57] ABSTRACT

A improved process for depolymerizing a poly(alpha-hydroxycarboxylic acid) to its corresponding dimeric cyclic ester is disclosed. The process comprises:

(i) depolymerizing the poly(alpha-hydroxycarboxylic acid) to its corresponding dimeric cyclic ester by heating the poly(alpha-hydroxycarboxylic acid) in a reaction zone at a temperature and pressure at which the poly(alpha-hydroxycarboxylic acid) is molten;

(ii) forming a vapor product stream containing the dimeric cyclic ester;

(iii) removing the vapor product stream from the reaction zone; and (iv) recovering the dimeric cyclic ester from the product stream; the improvement comprising: adding the dimeric cyclic ester to step (i) in the ratio of 0.01 to 0.5 part by weight of dimeric cyclic ester per part by weight of the poly(alpha-hydroxycarboxylic acid).

22 Claims, No Drawings

RECOVERY OF HYDROXYCARBOXYLIC ACID VALUES FROM POLY(HYDROXYCARBOXYLIC ACIDS)

FIELD OF THE INVENTION

This invention relates to an improved process for depolymerizing polymers and copolymers of such hydroxycarboxylic acids as glycolic, lactic and the like acids and recovering the hydroxy carboxylic values produced thereby in the form of cyclic esters.

More specifically, it relates to such process conducted in the presence of a liquid phase comprising a cyclic ester.

It further relates to a recycle depolymerization process wherein high molecular weight solid poly(alpha-hydroxycarboxylic acids) are recycled for depolymerization and the recovery of their hydroxy carboxylic values for reuse as dimeric cyclic esters.

DESCRIPTION OF RELATED PRIOR ART

The depolymerization of poly(hydroxycarboxylic acids), hereinafter polyhydroxycarboxylic acids (PHA), to lower molecular weight and volatile cyclic esters, including dimeric cyclic esters, is old in the art. It is also known that cyclic esters such as lactide, glycolide and the like are polymerizable to such PHAs as polylactic acid (PLA, polylactide), polyglycolic acid (PGA, polyglycolide) and copolymers thereof, useful in the manufacture of a variety of shaped articles.

An important property of these polymers is that they are slowly hydrolyzable and thereafter biodegradable to environmentally benign by-products. Consequently, high molecular weight PHA polymer shaped articles are finding increasing application as replacements for polystyrene and other non-degradable polymers in products that will degrade in a landfill, such as fast food containers (Sinclair et al., WO90/01521, Feb. 22, 1990).

While this is a significant step in minimizing litter and landfill disposal problems, discarding high molecular weight polyhydroxy acid articles for natural destruction by hydrolysis and biologic degradation has the cost penalty of discarding the valuable polyhydroxy acid.

Thus, there is a need for an economical method to recover for reuse the hydroxy carboxylic acid content of this source of insoluble waste material and avoid burdening landfills with this waste.

The most economical routes for PHA production start with the acid, e.g., lactic acid. The acid is converted to an oligomer thereof, i.e., a relatively low molecular weight polymer, which is generally a viscous liquid or low-melting solid. The oligomer is then depolymerized to the corresponding dimeric cyclic ester, e.g., lactide. The cyclic ester is then subjected to ring-opening polymerization conditions to obtain a solid high molecular weight PHA, e.g., PLA for the manufacture of shaped articles.

The depolymerization step of the above sequence is generally effected by heating the polymer at elevated temperatures effective to form a vapor product stream containing the cyclic ester, which is then recovered from the product stream, as disclosed, for example, in Gruter, U.S. Pat. Nos. 1,095,205; Lowe 2,668,162; Selman 3,322,791; Bhatia 4,835,293; Bhatia 5,023,349; Aigner et al. 4,990,222; Muller 5,053,522; and Moser, Ger. Pat. 1,083,275.

Normally and conveniently, the polymer used in the depolymerization process for cyclic ester production is a relatively low molecular weight oligomer. However, Moser, Ger. Pat. 1,083,275, discloses that optically active and inactive lactides can be produced in good yields by depolymerizing high polymer polylactic acids (obtained by polymerizing the corresponding lactides) at a bath temperature of 190° to 260° C., preferably in vacuo and in the presence of certain metals or compounds thereof. Example 6 discloses that a PLA having a relative viscosity of 4.3, measured as a 1% benzene solution, was depolymerized to lactide at 250° C. in the presence of tin (II) oxide in about 90% yield.

The depolymerization processes of the art, wherein an oligomeric or higher polymeric PHA such as PLA is heated at elevated temperatures in the presence or absence of a catalyst, suffer in that depolymerization to cyclic ester tends to be slow, attributable to the difficulty of getting heat (thermal energy) rapidly and uniformly distributed throughout the polymeric mass. Side reactions occur, believed at least in part due to the formation of localized hot spots within the depolymerization mass, including decomposition of the polymer to charred and tarry products and resulting in difficult to handle reactor heels. The heat distribution problem is more severe with solid/higher molecular weight polymers than with liquid/lower molecular weight polymers as they tend to form more viscous melts. In general, the higher the degree of polymerization and the higher the melting point of the polymer, the more viscous the molten mass.

Although the addition of extraneous substances has been suggested to ameliorate this problem (Bellis, U.S. Pat. Nos. 4,727,163; Bhatia 5,091,544) their use is not entirely satisfactory on a commercial scale as they add to the overall cost of the process and pose potential environmental contamination issues.

A need exists for an improved process for depolymerizing PHAs to cyclic esters, in particular such process for recycling spent or discarded high molecular weight PHAs, in particular PLAs, for the recovery of their hydroxycarboxylic acid values.

SUMMARY OF THE INVENTION

The invention is a process for depolymerizing a poly(alpha-hydroxycarboxylic acid) to its corresponding dimeric cyclic ester, the process comprising:
 (i) depolymerizing the poly(alpha-hydroxycarboxylic acid) to its
 corresponding dimeric cyclic ester by heating the poly(alpha-hydroxycarboxylic acid) in a reaction zone at a temperature and pressure at which the poly(alpha-hydroxycarboxylic acid) is molten;
 (ii) forming a vapor product stream containing the dimeric cyclic ester;
 (iii) removing the vapor product stream from the reaction zone; and
 (iv) recovering the dimeric cyclic ester from the product stream; the improvement comprising: adding the dimeric cyclic ester to step (i) in the ratio of 0.01 to 0.5 part by weight of dimeric cyclic ester per part by weight of the poly(alpha-hydroxycarboxylic acid).

The polyhydroxycarboxylic acid being depolymerized preferably comprises a major proportion of a poly (alpha-hydroxycarboxylic acid), and the liquid/liquefied cyclic ester in contact with the polymer is preferably a dimeric cyclic ester, more preferably a dimeric cyclic ester corresponding to the alpha-hydroxycarboxylic acid units of the polymer. In other words, the liquid cyclic ester in contact with the polymer during depolymerization preferably corresponds to the cyclic ester depolymerization product.

The cyclic ester can be added initially or during the depolymerization reaction, including by condensing (liquefying) at least a portion of the vapor product stream containing cyclic ester and returning a portion of the cyclic ester to the reaction mass, or by injecting, as by sparging, liquid cyclic ester into the depolymerization mass as needed to lower the viscosity of the mass and thereby facilitate the process. [Viscosities of the depolymerization mass at various temperatures are conveniently determined by capillary rheometry, a standard method.]

The invention depolymerization and polyhydroxy acid recycle process provides for smoother and faster melting of the polymer and far smoother and more rapid depolymerizations and produces cyclic esters in high yields while minimizing yield-consuming side reactions. The liquid cyclic ester in contact with the polymer to be converted to cyclic ester facilitates the dissolution of and/or melting of solid PHAs at operating (depolymerization) temperatures, rendering them more fluid and more amenable to thermolysis to cyclic esters. It also serves as a means of distributing depolymerization catalyst as well as thermal energy rapidly and uniformly throughout the depolymerizing mass.

The use of cyclic esters in the recovery of hydroxycarboxylic values from PHAs directly as cyclic esters is not dependent on extraneous solvents, reactants or other agents, and thereby simplifies while facilitating the depolymerization process.

Thus, the invention comprises a depolymerization process for rapidly and economically recovering the valuable hydroxycarboxylic content of depolymerizable polyhydroxycarboxylic acids (PHAs) in the form of cyclic esters for reuse as starting materials in the manufacture of a variety of products based thereon, including high polymer shaped articles for non-medical as well as medical uses well known in the art. Avoided thereby is the prior need for landfill and biodegradation of PHA products such as fast food plates, cups, eating utensils and containers.

DESCRIPTION OF THE PREFERRED EMBODIMENTS

The invention depolymerization process is applicable to a wide variety of normally liquid or solid poly(hydroxycarboxylic acid) (PHAs) that are depolymerizable to cyclic esters under depolymerization conditions such as those described in the patents referenced above. The PHAs include those prepared by condensation polymerization of the corresponding aliphatic hydroxycarboxylic acids, with elimination of water, as well as those prepared by ring-opening polymerization of a suitable cyclic ester of such a hydroxycarboxylic acid, generally in the presence of a catalyst.

The hydroxy acid units of the PHAs correspond to hydroxycarboxylic acids wherein the hydroxyl group is at a carbon atom positioned alpha or higher to the carboxyl group. Preferably, the hydroxyl group is alpha, as in lactic acid, and when other than alpha is preferably gamma or higher, as in gamma-hydroxybutyric acid, and normally is not higher than epsilon, as in epsilon-hydroxycaproic acid. Preferably, too, PHA units corresponding to alpha-hydroxycarboxylic acids predominate, and preferably are lactic and/or glycolic units.

The lactic units may be L-, D-, racemic L-, D-, meso- or a mixture of any two or more thereof.

The molecular weight of the PHA can vary widely from about 400 to about 500,000, e.g., from that of an oligomer (about 400 to about 2000), through that of an intermediate polymer (greater that about 2000 to about 10,000) to that of a high polymer (greater than about 10,000 and generally from about 15,000 to 500,000 molecular weight).

In a preferred aspect of the invention, the PHAs are normally solid high molecular weight homo- or copolymers of lactide, the dimeric cyclic ester of lactic acid, namely 3,6-dimethyl-1.4-dioxane-2,5-dione, or of glycolide, the dimeric cyclic ester of glycolic acid, namely 1,4-dioxane-2,5dione. The copolymers may contain minor proportions (generally less than 30% by weight) of copolymerized units derived from other hydroxy carboxylic acids, for example from such comonomers as: epsilon-caprolactone; delta-valerolactone; 1,4-dioxane-2-one; 1,4-dioxepane-2-one; 1,5-dioxepane-2-one, gamma-butyrolactone; beta, beta-dimethyl-propiolactone; and trimethylene carbonate, i.e., 1,3-dioxane-2-one. Representative depolymerizable PHAs, including PLA and PGA polymers and copolymers are disclosed in McLain et al., U.S. Pat. Nos. 5,028,667, Nieuwenhuis et al. 5,053,485; Rosensaft et al. 4,300,565; Vert et al. 4,279,249; Schneider 2,703,316; Schmitt et al. 3,297,033; Lange 4,471,077; Murdoch et al. 4,719,246; Nijenhuis et al., WO 91/16368 and Sinclair et al., WO 90/01521.

The cyclic ester employed in the depolymerization process can vary widely as to its composition provided it is meltable at or below depolymerization temperatures and is effective to lower the viscosity of the molten polymer. The cyclic ester desirably corresponds to at least one of the hydroxycarboxylic units in the polymer, preferably to the major such unit to simplify the work-up of the vapor product stream into its components. The cyclic ester can be a simple ester (lactone), O—G—CO, wherein G is an alkylene or oxaalkylene radical having 3 to 7, preferably 4 to 5 atoms, in the chain. Preferred oxaalkylene radicals are those wherein the oxa atom, i.e., —O—, is non-terminal. Examples of simple lactones are: delta-valerolactone, epsilon-caprolactone, 1,4-dioxane-2-one, 1,4-dioxepane-2-one, 1,5-dioxepane-2-one and 1,3-dioxane-2-one (trimethylene carbonate).

Preferred cyclic esters are dimeric cyclic ester, O—($CR_1R_2$)CO—O($CR_1R_2$)CO, where $R_1$ and $R_2$ are independently hydrogen or lower alkyl, preferably methyl when other than hydrogen; in particular $R_1$ and $R_2$ are hydrogen or methyl as in glycolide ($R_1=R_2=H$) and lactide ($R_1=H$, $R_2$ =methyl) with lactide preferred, in particular D-, L- or D, L(racemic)-lactide, especially for use in the depolymerization of a PHA such as PLA wherein units corresponding to the formula —OCH($CH_3$)—CO—, derived from lactic acid or lactide, predominate.

In carrying out the process, the cyclic ester is mixed with the polymer to be depolymerized, which if solid is preferably in comminuted form, in amounts sufficient (a) to form a slurry or solution of the polymer in the cyclic ester and (b) to lower the viscosity of the resulting polymer-cyclic ester mixture when molten to below the viscosity of the polymer alone when molten at the same temperature, below the depolymerization temperature. In one preferred mode of operation, the polymer is added to a molten bath of cyclic ester or cyclic ester plus polymer.

To effect depolymerization the cyclic ester-polymer mixture, which can be one-phase or two-phase, is heated, with or without agitation, to melting and depolymerization temperatures, with the temperature, pressure and other conditions if necessary, as described below, adjusted such that an effective viscosity-lowering-quantity of cyclic ester remains in the depolymerizing mixture while another quantity of cyclic ester is being removed from the depolymerizing mixture as vapor product.

Maintaining sufficient liquid cyclic ester in contact with the depolymerizing polymer can be accomplished by (a) operating at a pressure at which the boiling point of the cyclic ester to be recovered as vapor product is substantially equal to the depolymerization temperature, (b) condensing a portion of the cyclic ester out of the vapor product stream as product and (c) returning a portion of condensed liquefied cyclic ester to the depolymerization mass as needed to maintain a lowered viscosity level in the mass.

If desired, a polymer such as a PLA can be added in portions to a cyclic ester such as lactide maintained under reflux at depolymerizing temperatures and pressures, and lactide removed as fast as it is formed via depolymerization while returning a sufficiently fluidizing amount of condensed lactide to the polymer in the reactor as needed. Condensate cyclic ester can be returned as downcoming reflux or as a separate stream via a separate pipeline (heated if necessary to maintain the condensate liquid) and injected, e.g., sparged through a filtered disc, into the depolymerizing mass, below its surface. Alternately, the polymerization mass can be continuously removed from and recycled to the reactor by means of an external pump, with the recycle line and pump appropriately heated, and with cyclic ester being fed to the recycle line as needed to maintain a desired lowered viscosity in the reactor.

The reflux ratio, i.e., the liquefied cyclic ester condensate return to takeoff ratio, can vary widely; however, in the interest of recovering depolymerization cyclic ester as rapidly as possible the return takeoff ratio should be as small as practicable, even to a point where the mount being returned to the reactor is barely perceptible. Since the pressure at the surface of the depolymerizing mixture is greater than at the condenser/product takeoff level, even a barely perceptible level of return ensures the presence of liquid state cyclic ester in the depolymerizing polymer. The proportion of liquid phase cyclic ester in the reactor can be controlled by varying the return to takeoff ratio as desired or by operating at a fixed ratio and increasing the distance between the polymer surface and the condenser takeoff, even where the takeoff is barely perceptible, since, in general the greater this distance the greater the pressure drop between the two points and the larger the proportion of liquid phase cyclic ester in the polymer composition.

In an alternative embodiment, the cyclic ester is mixed with the polymer at depolymerization temperatures and pressures, such that the cyclic ester boiling point is exceeded. The added cyclic ester is conveniently the same as that produced from the polymer. In such case, to maintain a liquid cyclic ester presence in the depolymerizing polymeric mass, molten cyclic ester, preheated to a temperature close to the depolymerization temperature, is injected, as by sparging through a filtered disc, below the surface of the polymer so that the cyclic ester is in intimate contact with the polymer, if only momentarily, before it vaporizes and exits the polymeric mass along with vaporized cyclic ester formed via depolymerization. The molten cyclic ester feed can be intermittent or substantially continuous; the rate of feed is preferably adjusted such that the amount fed in a given time period is less than the total amount of cyclic ester removed from the reaction mass in the vaporized product stream during that time.

In a variant of the above embodiment, the injected cyclic ester is chosen sufficiently higher-boiling than that produced in the depolymerization reaction to allow a sufficient quantity of it to remain in the reaction mass while the depolymerization cyclic ester is volatilized therefrom and removed, by fractional distillation if necessary, to obtain depolymerization product cyclic ester as the predominant cyclic ester including substantially free of the higher-boiling cyclic ester.

Injecting/sparging cyclic ester into the depolymerizing polymer not only provides a means of introducing liquid cyclic ester into it, but provides other advantages as well: it serves as a means of agitating the polymeric mass and, is preferably being chosen such that it vaporizes at depolymerization temperature and pressures, it also serves as a means of facilitating the vaporization and removal of depolymerization cyclic ester as formed. Agitating the mass in this way provides for a more uniform input of heat into it and therefore a smoother depolymerization process, whereby localized overheating leading to decomposition and charring of the mass is largely avoided.

Further, injecting/sparging cyclic ester into the depolymerizing polymer enables the process to be operated at low reduced pressures-that is, pressures well below the pressure exerted by the cyclic ester product at the depolymerization temperature. In such embodiment, the product cyclic ester is above its boiling point and is vaporized/flashes off as formed. This allows the polymer conversion rate and the cyclic ester recovery rate to be maximized.

The quantity of cyclic ester needed to lower the viscosity of a PHA to a desired extent varies with the cyclic ester and the polymer. For example, a typical high molecular weight normally solid optically active polylactic acid, PLA, melts at about 180° C. and exhibits a viscosity of from about 10 to 30 kilopoises at the melt depending upon its molecular weight and total composition. A typical high molecular weight polyglycolic acid, PGA, on the other hand, melts at about 220° C., and PGA-PLA copolymers melt somewhat lower, e.g., 207° C. for a 90 GA-10 LA copolymer, with the viscosities at the melt being in general somewhat greater for the higher melting than the lower melting materials. In general, it is desired to reduce the viscosity at least about 10% of the initial valve, preferably at least about 20% with not more than 30% needed. Incorporating a cyclic ester such as lactide and/or glycolide into the polymer tends to lower the melting point as well as the viscosity. Incorporating a lactide, mp. 96° C., for example, into PLA having a viscosity of about 14,000 poises at 180° C., in an amount of 0.01 parts per part of polymer, lowers the viscosity to about 1,250 poises and thereby renders the composition more fluid and easier to handle, e.g., pump into the reaction zone, and facilitates the depolymerization to volatile cyclic ester (lactide) as discussed above.

The cyclic ester is normally used in amounts of at least about 0.01 part per part of polymer, more usually at least about 0.05 part per part and preferably about 0.1 to 0.5 part per part. Smaller proportions of cyclic ester do not always provide the intended result while larger proportions appear unnecessary. In general, the greater the proportion of the cyclic ester in the mixture the lower the viscosity and the more effective the cyclic ester for the purposes of the invention. Operable and optimum proportions of the cyclic ester are readily determined by trial for any combination of cyclic ester and PHA.

Whatever the embodiment, the proportion of liquefied cyclic ester in the depolymerizing polymer can be allowed to decrease as the depolymerization progresses with decrease in polymer molecular weight since the viscosity of the molten mass also tends to decrease as the degree of polymerization decreases with time.

Suitably effective temperatures and pressures for converting polymer to cyclic ester in accordance with the method of the invention can vary widely, with optimum conditions depending largely on the polymer-cyclic ester composition. Typical depolymerization temperature-pressure combinations involve temperatures for polylactides, polyglycolides and copolymers thereof in the range of from about 200° to about 270° C. with commensurate pressures in the range of from about 10 to about 900 mm Hg. A typical PLA-lactide diluent process is conducted, for example, at reduced pressures of from about 200 to 300 mm Hg and depolymerization temperatures of from about 210° to 230° C. with the temperature and pressure coordinated to maintain vapor product stream lactide in equilibrium with liquid phase lactide in the depolymerization mass. A comparable PGA-glycolide embodiment can be similarly carried out but with somewhat higher temperatures, such as 230° to 270° C., required at the indicated pressures.

The process of this invention is generally conducted in the presence of a catalyst, which may be carried in the polymer before or after it is fed to the reactor. The catalyst can be any catalyst of the an suitable for promoting the thermolysis of the polymers to cyclic esters. Suitable catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide $Sb_2O_3$. Preferred herein are Sn (II) carboxylates, especially those that are soluble in the molten polymer exemplified by stannous bis(2-ethylhexanoate), commonly referred to as stannous octoate.

The catalyst is employed in catalytically-effective amounts, which can vary widely depending upon the particular feed material employed and the reaction conditions. The optimum catalytically-effective amounts for any particular system can readily be determined through trial runs. For example, with stannous octoate as the catalyst, the quantity of catalyst will generally be such that the reaction mass contains from about 0.01 to about 5% by weight, usually from about 0.3 to 3% and for best results, at least about 1%. High catalyst loadings are desirable because polymer residence time decreases with increases in the initial catalyst concentration, thereby improving the cyclic ester production rate.

It will be appreciated by those skilled in the art that the catalysts are cyclic ester polymerization catalysts as well as depolymerization catalysts for the production of cyclic esters. In accordance with the invention, the cyclic ester depolymerization product is removed from the depolymerization reactor substantially as fast as it is formed and vaporized while at the same time maintaining a residual quantity of liquid cyclic ester in contact with the polymeric mass utilizing the techniques described above.

The reactor design and configuration are not critical provided there are means for providing a molten or particulate solid polymer feed in the depolymerization zone, means for introducing liquid (liquefied) cyclic ester as needed, means for heating the depolymerization zone, means for removing a vapor product stream comprising the cyclic ester to be recovered from the upper end of the reactor and means for collecting unconverted polymer, if any, from the lower end of the reactor. Thus, the reactor may be any of those known in the art for carrying out the depolymerization reaction but modified accordingly to accommodate the cyclic ester polymer-fluidizing component of the invention.

The vapor product stream exiting the reactor normally comprises the dimeric cycle ester and other volatiles, including open-chain hydroxycarboxylic acids (e.g., lactic acid, lactoyllactic acid, etc.). The condensed vapor product is readily separated into its constituents using known methods such as distillation, extraction, crystallization, etc.

The unconverted, i.e., incompletely converted oligomer stream exiting the lower end of the reactor can be recovered. It is often suitable for reuse as feedstock to the depolymerizer, preferably in a mixture with fresh polymeric feed material and cyclic ester.

EXAMPLES

EXAMPLE 1 a. An oligomer of L-lactic acid is prepared by heating 750 grams 88% L-lactic acid containing 0.3 percent stannous octoate at temperatures up to 180° C. with removal of water until the product has a degree of polymerization of about 10 corresponding to a molecular weight of about 738.

b. 500 Grams of the still molten oligomer (15° C.) is mixed with 50 grams of L-lactide and the mixture is transferred to a one-plate reduced pressure still having a reboiler surmounted by an oil heated vertically-arranged reflux condenser equipped with heated means for removing lactide distillate under reflux.

The distillation apparatus is evacuated to about 100 mm Hg while the condenser and lactide takeoff line are heated with 110° C. circulating oil.

The oligomer-lactide mixture in the reboiler is gradually heated to 210° to 215° C. and the pressure adjusted to between about 100 and 140 mm Hg until lactide is beginning to condense and reflux in the column, whereupon lactide takeoff is begun and a slight reflux is established and maintained by controlling the takeoff rate and the temperature and pressure. The process is continued until substantially all the oligomer is converted to lactide and recovered as distillate.

EXAMPLE 2

Depolymerization step b of Example 1 is repeated with a well-mixed mixture of 50 grams of powdered L-lactide, top. 96° C., 500 grams of a powdered poly(L-lactic acid) having a molecular weight of about 200,000 and melting at 175° C. and 1.5 grams of stannous octoate.

Heating of the mixture is gradual until the mixture in the reboiler melts. It is then rapidly increased to and held at between 210° and 220° C. to establish a strong reflux, and liquefied lactide is removed at a high takeoff to return ratio. The process is continued until substantially all the polymer is convened to volatilized products and lactide is recovered therefrom.

EXAMPLE 3

The process of Example 2 is repeated except that (a) lactide is omitted from the mixture, (b) the reactor is modified to contain a tubular means terminating in a fritted disc for sparging molten L-lactide beneath the surface of the polymer-catalyst mixture when molten, and (c) the reactor is evacuated to 15–20 mm Hg. When lactide is observed condensing in the condenser at the depolymerization temperature, sparging of 75 grams of 180° C. L-lactide at a rate of 1.5 grams/min is begun and the lactide is taken off as fast as it can be condensed. The process is continued until substantially all the polylactic acid has been converted to a vapor product stream and its lactide content recovered therefrom.

We claim:

1. In a process for depolymerizing a poly(alpha-hydroxycarboxylic acid) to its corresponding dimeric cyclic ester, the process comprising:
   (i) depolymerizing the poly(alpha-hydroxycarboxylic acid) to its corresponding dimeric cyclic ester by heating the poly(alpha-hydroxycarboxylic acid) in a reaction zone at a temperature and pressure at which the poly(alpha-hydroxycarboxylic acid) is molten;
   (ii) forming a vapor product stream containing the dimeric cyclic ester;
   (iii) removing the vapor product stream from the reaction zone; and
   (iv) recovering the dimeric cyclic ester from the product stream; the
   improvement comprising: adding the dimeric cyclic ester to step (i) in the ratio of 0.01 to 0.5 part by weight of dimeric cyclic ester per part by weight of the poly(alpha-hydroxycarboxylic acid).
2. The process of claim 1 wherein the alpha-hydroxycarboxylic acid is selected from the group consisting of glycolic acid and lactic acid.
3. The process of claim 1 wherein the poly(alpha-hydroxycarboxylic acid) is poly(lactic acid).
4. The process of claim 1 wherein the poly(alpha-hydroxycarboxylic acid) is poly(L-lactic acid).
5. The process of claim 1 wherein step (i) is carried out at a temperature of 180° C. to 220° C.
6. The process of claim 1 wherein a catalyst that promotes the thermolysis poly(alpha-hydroxycarboxylic acid)s to cyclic esters is present in the reaction zone.
7. The process of claim 6 wherein the catalyst is stannous octonate.
8. The process of claim 6 wherein the poly(alpha-hydroxycarboxylic acid) has a molecular weight of 400–500,000.
9. The process of claim 8 wherein the ratio of added dimeric cyclic ester to poly(alpha-hydroxycarboxylic acid) is 0.1 to 0.5.
10. The process of claim 9 wherein the alpha-hydroxycarboxylic acid is selected from the group consisting of glycolic acid and lactic acid.
11. The process of claim 9 wherein the poly(alpha-hydroxycarboxylic acid) is poly(lactic acid).
12. The process of claim 1 wherein the dimeric cyclic ester is added to step (i) by recycling a portion of the dimeric cyclic ester recovered in step (iv) to the reaction zone.
13. The process of claim 12 wherein step (i) is carried out at a temperature of 180° C. to 220° C.
14. The process of claim 12 wherein the alpha-hydroxycarboxylic acid is selected from the group consisting of glycolic acid and lactic acid.
15. The process of claim 14 wherein a catalyst that promotes the thermolysis poly(alpha-hydroxycarboxylic acid)s to cyclic esters is present in the reaction zone.
16. The process of claim 12 wherein the poly(alpha-hydroxycarboxylic acid) is poly(lactic acid).
17. The process of claim 12 wherein the poly(alpha-hydroxycarboxylic acid) has a molecular weight of 400–500,000.
18. The process of claim 17 wherein the ratio of added dimeric cyclic ester to poly(alpha-hydroxycarboxylic acid) is 0.1 to 0.5.
19. The process of claim 18 wherein the alpha-hydroxycarboxylic acid is selected from the group consisting of glycolic acid and lactic acid.
20. The process of claim 18 wherein step (i) is carried out at a temperature of 180° C. to 220° C.
21. The process of claim 18 wherein the poly(hydroxycarboxylic acid) is poly(lactic acid).
22. The process of claim 18 wherein the poly(alpha-hydroxycarboxylic acid) is poly(L-lactic acid).

* * * * *